United States Patent [19]

Cross

[11] Patent Number: 5,494,046
[45] Date of Patent: Feb. 27, 1996

[54] PATIENT MONITORING SYSTEM

[75] Inventor: Alan W. Cross, Denton, Nebr.

[73] Assignee: Senior Technologies, Inc., Lincoln, Nebr.

[21] Appl. No.: 88,733

[22] Filed: Jul. 7, 1993

[51] Int. Cl.⁶ .................................................. A61B 5/103
[52] U.S. Cl. .......................................... 128/782; 340/573
[58] Field of Search ................................... 128/774, 782; 340/573, 575

[56] References Cited

U.S. PATENT DOCUMENTS

| 4,020,482 | 4/1977 | Feldl | 128/782 |
|---|---|---|---|
| 4,263,586 | 4/1981 | Nicholas | 128/782 |
| 4,336,533 | 6/1982 | Wettach | 128/782 |
| 4,583,084 | 4/1986 | Henderson et al. | 128/782 |

Primary Examiner—Max Hindenburg
Attorney, Agent, or Firm—Vincent L. Carney

[57] ABSTRACT

To monitor a patient, a combined allegator clip and switch is fastened to the patient by a cord having a length of between five inches and five feet. The other end of the cord is connected to a switch which is activated when the patient moves beyond the length of the cord to cause a message to be announced. If the allegator clip is removed, another circuit activates the alarm to play the voice message and provide an alarm to a caretaker at a remote station. The fastener is an alligator clip having first and second jaws and a spring for biasing said first and second jaws together, whereby said alligator clip may be fastened to clothing. When the jaws are separated by clothing, two conductors are separated but when the jaws contact each other, the conductors are closed to activate the voice message.

10 Claims, 4 Drawing Sheets

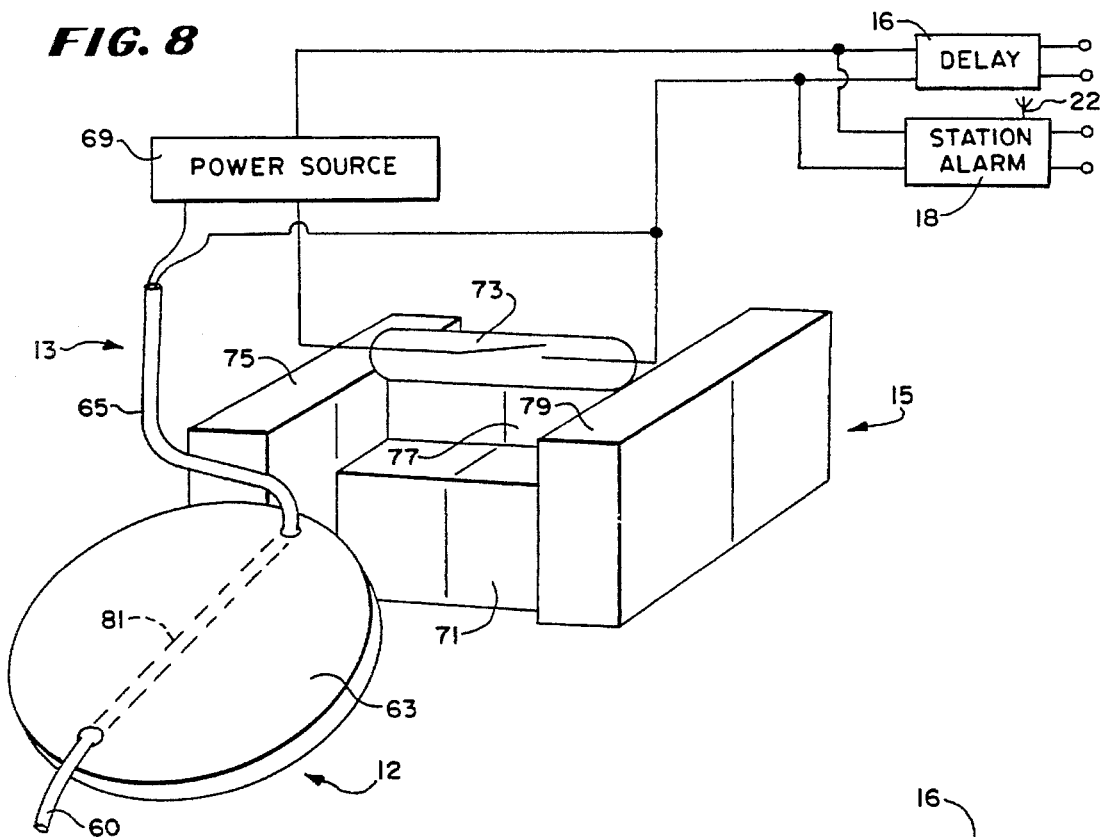
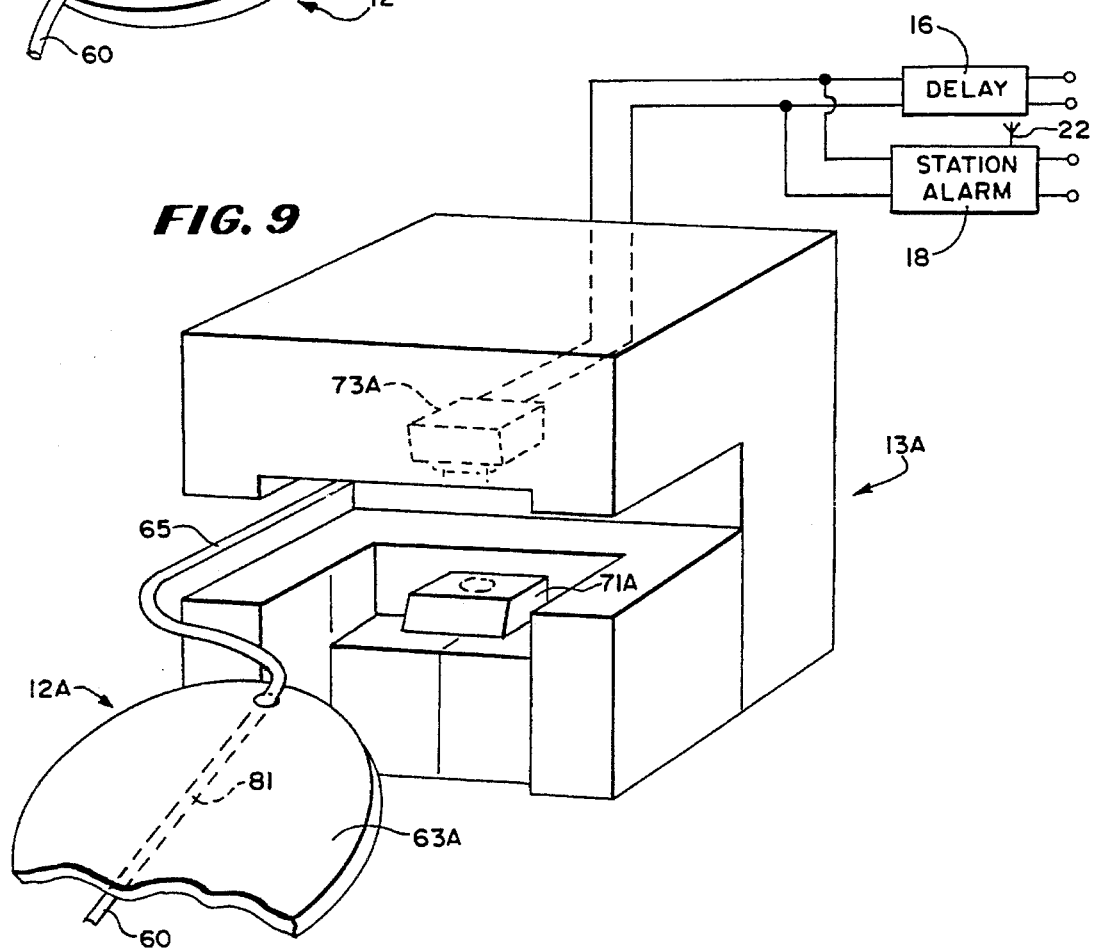

PATIENT MONITORING SYSTEM

BACKGROUND OF THE INVENTION

This invention relates to patient monitoring systems and particularly to patient monitoring systems in which movement of a patient beyond a certain distance provides an alarm or a warning.

In one class of patient monitoring system, a fastener is connected to a monitoring housing by a cord or other device having a fixed length so that if the fastener moves beyond that length, the monitoring housing is activated. The fastener is connected to a patient such as to the clothing of a patient by a clip so that, if the patient moves beyond a fixed distance such as by slumping from a wheelchair onto the floor or moving from a bed, the monitoring housing provides an alarm.

In a prior art monitoring system of this type, the end of the cord opposite to the fastener is loosely fitted into the monitoring housing so that, when the patient moves away from the monitoring housing a distance greater than the length of the cord, that end is pulled free. When the end is pulled free from the monitoring housing, an alarm is given. Prior art systems of this type are disclosed in U.S. Pat. Nos. 4,577,185, 4,858,622, and 4,583,084 and systems of this type are on sale under the trademark, TABS, by Wanderguard, Inc., a division of Senior Technologies, Inc., located at 941 "O"Street, Suite 205, Lincoln, Neb. 68508.

This type of prior art patient monitoring system has several disadvantages, such as for example: (1) from time to time the fastener falls loose from the patient or is removed by the patient so that the system fails; and (2) the patient may hear or see the alarm and be unduly excited by it or the patent may not hear the alarm but continue to leave the bed or chair to which the patent is confined.

Spring loaded fasteners are known in the prior art and are generically referred to as alligator clips. At least one type of prior art alligator clip provides an electrical signal when closed. Such an alligator clip is disclosed in U.S. Pat. No. 4,616,113 as part of a fabric theft warning device. This prior art alligator clip with a sensor is relatively expensive because it has a special mechanism to prevent a thief from slipping a card between the jaws of the alligator clip when the fabric is removed and thus being able to remove the fabric without giving the alarm.

SUMMARY OF THE INVENTION

Accordingly, it is an object of the invention to provide a novel patient monitoring system.

It is a further object of the invention to provide a novel fastener which may complete a circuit under certain conditions.

It is a still further object of the invention to provide a patient monitoring system which does not unduly alarm the patient but nonetheless provides a useful message to the patient.

It is a still further object of the invention to provide a patient monitoring system that is difficult for the patient to defeat either intentionally or accidentally.

In accordance with the above and further objects of the invention, a monitoring system detects when the patient moves inappropriately such as falling from a wheelchair or leaving a bed to which the patient is confined. In the preferred embodiment, the monitoring system first initiates the alarm sequence and then provides a quiet and soothing warning or request. It may be a request not to move for example. The monitoring system may also illuminate a warning light or provide another audible attention getter for the caretaker at the location of the patient and/or at a remote location.

More specifically, the monitoring system includes a cord fastened at one end to a monitoring housing and at the other end to a clip, such as an alligator clip. The alligator clip has insulated jaws separating a conductor combination from the clip itself. The conductor combination moves with the jaws so that the clip fastens the cord to the clothing of a patient at one end of the cord and to an alarm housing at the other end of the cord.

When the patient moves beyond the length of the cord such as by falling or the like, a switch changes condition either from an open position to a closed position or a closed position to an open position and the monitoring system issues an alarm. The alarm may be located in the vicinity of the patient or at a remote location or both. If there is an alarm at the patient's location, it will preferably sound just before a voice message to the patient but in some embodiments, the voice message may play simultaneously with or before the alarm. The voice message may be to soothe the patient or to provide instructions such as for the patient to remain stationary until an attendant appears.

The alligator clip switch may either be a primary sensing switch or a backup switch. If it is a primary switch, when the patient pulls free and the jaws close, the conductors close or open a circuit to the monitoring housing which initiates the alarm and the voice message to the patient. When used as a backup switch, it is intended to protect against unauthorized removal such as for example to avoid the triggering of an alarm by a patient being monitored.

The patient monitoring system of this invention has several advantages, such as for example: (1) it is difficult for the patient to defeat; (2) it provides a tailored message to the patient rather than an alarm signal which might cause an undesirable effect; (3) it is relatively flexible in the nature of the warning or message to the patient, the sequence of the alarm and message and the location or locations of the alarm to the caretaker of the patient.

SUMMARY OF THE DRAWINGS

The above noted and other features of the invention will be better understood from the following detailed description when considered in connection with the accompanying drawings, in which:

FIG. 8 is a simplified partly perspective and partly schematic view of a portion of the embodiment of FIG. 7;

FIG. 9 is a simplified, fragmentary, partly perspective and partly schematic view of another embodiment of the invention;

DETAILED DESCRIPTION

Figure 1:
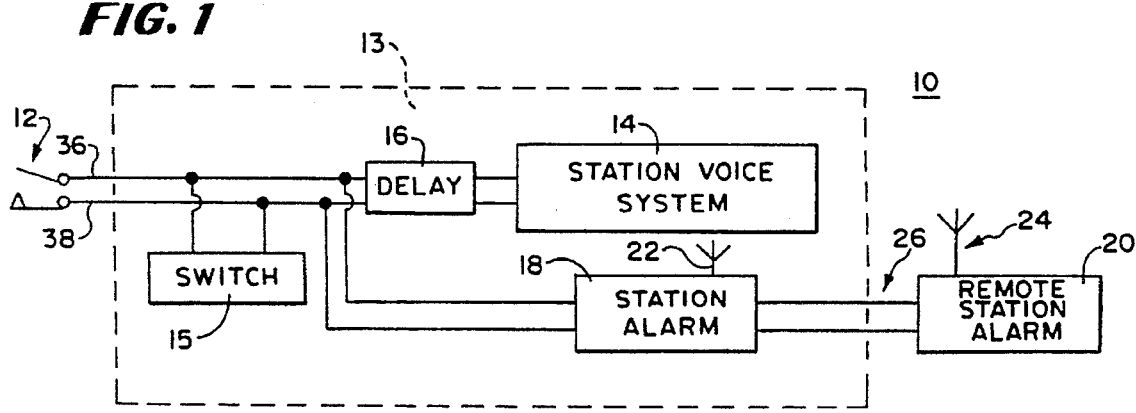
FIG. 1 is a block diagram of a patient monitoring system in accordance with the invention.

In FIG. 1, there is shown a block diagram of a patient monitoring system 10 having a first switch 12, a patient-station monitoring housing 13 and a remote station alarm 20. The patient station monitoring housing 13 includes a voice record system 14, a second switch 15, a time delay 16 and a station alarm 18.

The first and second switches 12 and 15 are each electrically connected to the voice system 14 through the delay line 16 to initiate playing of a message to the patient and any nearby caretaker when the switch is activated and to the station alarm 18 to provide a warning to the caretaker immediately if the caretaker is near. The station alarm 18 may illuminate a lamp or provide another warning and may transmit a signal either through a radio system shown at the antenna 22 or through conductors 26 to the remote station alarm 20 where it may be received by an antenna 24 or the conductor 26.

While in the embodiment of FIG. 1, alarms are provided before the message is played both near the patient and at a remote location, the alarm nearby from the station alarm 18 may be omitted and the signal transmitted directly to the remote station alarm 20 or the message may be played simultaneously with either or both the station 18 and remote alarm 20 or before either or both alarms. The voice system 14 may be any standard commercial arrangement such as are now commonly used to play a fixed message. In the preferred embodiment, the voice system is a single-chip, voice record/playback device, model 1SD1020A sold under the trademark DAST by Information Storage Devices, Inc., 2841 Junction Avenue, Suite 204, San Jose, Calif. 95134.

With this arrangement, if a patient moves beyond the length of the cord, such as for example by falling from a chair, wheelchair or bed or attempts to leave the wheelchair, chair or bed, a voice message may be given to him or her and alarms are provided to the caretaker. This can be done through the switch 15 within the housing 13 which is activated as the cord pulls on that end. On the other hand, if the cord is jammed so as to not activate the switch 15 or if the patient attempts to remove the alligator clip switch at 12, the warnings and voice messages are still played. Thus, the two parallel switches 12 and 15 cooperate together to provide a tamper free and anti-jam warning device and message device.

Figure 2:
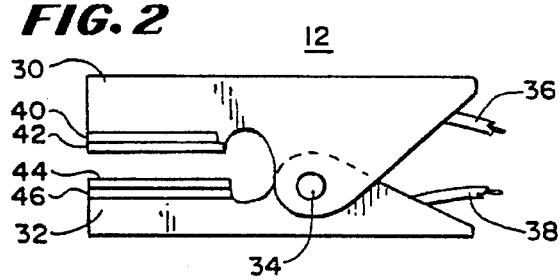
FIG. 2 is an elevational view of a fastener used in the embodiment of FIG. 1.

In FIG. 2, there is shown an elevational view of a switch 12, which is formed as part of a fastener, such as a fastener that might be used in the manner of an alligator clip to fasten to the clothing of a patient. In the preferred embodiment, the switch 12 includes a first jaw 30, a second jaw 32, a pivot 34, a first insulated conductor 36 and a second insulated conductor 38. The first and second jaws 30 and 32 are spring biased together so that if they are not separated by clothing, the insulated conductors 36 and 38 are electrically connected to each other through the first and second jaws 30 and 32 but if clothing is between the jaws 30 and 32 so as to space them, the switch 12 is open. Of course, the contacts could be on the other side of the pivot 34 so that the switch would be open when the jaws are in contact and the switch would be closed when the jaws are open, in which case the open switch would trigger the alarm.

In the preferred embodiment, the first jaw 30 has at its bottom surface a first insulating layer 40 and a first conductive layer 42 and the second jaw 32 has on its surface facing the conductor 42 a second insulating layer 46 and a second conductive layer 44 arranged so that when the jaws are clamped together, the first conductive layer 42 electrically connects the second conductive layer 44 to close a circuit between the insulated conductors 36 and 38. These conductive layers, while being electrically connected to respective ones of the conductors 36 and 38, are insulated from the remainder of the alligator clip by the insulative layers 40 and 46.

Figure 3:
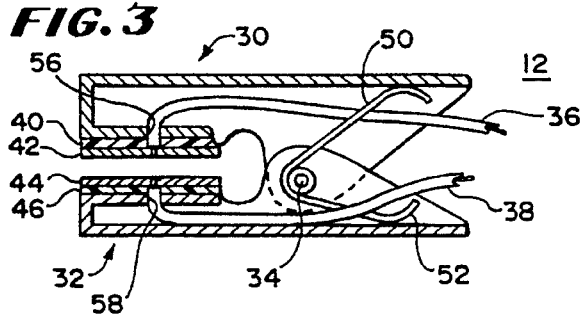
FIG. 3 is a sectional view of the fastener of FIG. 2.

As best shown in FIG. 3, which is a sectional view, the switch 12 includes a spring having legs 50 and 52 mounted to the pivot point at 34 and extending backwardly to bias the first and second jaws 30 and 32 together. Each of the first and second jaws includes a corresponding elongated outer leg, a corresponding flat front surface and a corresponding inwardly bent surface, with the inwardly bent surface being adapted to receive the first and second insulator layers 40 and 46 and the first and second conductive layers 42 and 44 respectively.

The first conductor 36 has its insulation removed at one end. The one end is inserted through aligned holes 56 in the inwardly turned end of the first jaw 30, first insulative layer 40 and conductive layer 42 and is electrically connected to the conductive surface 42. The uninsulated end of the conductor 36 and the conductive layer 42 are insulated from the jaw 30 by the insulative layer 40. The second insulated conductor 38 has its insulation removed at one end. The one end is inserted through aligned holes 58 in the second jaw 32, second insulative layer 46 and second conductive layer 44 and is electrically connected to the conductive layer 44. The conductor 38 and conductive layer 44 is insulated from the remainder of the jaw 32 by the insulative layer 46.

With this arrangement, when the elongated legs of the jaws 30 and 32 are released, the conductive layers 42 and 44 move together, and if there is no insulator between them, they contact each other to form an electrical circuit. If there is fabric of a patient's clothing between them, the jaws remain spaced and the circuit is closed.

Figure 4:
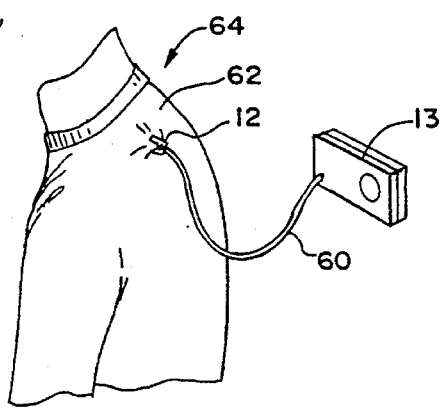
FIG. 4 is a fragmentary, simplified elevational view showing a manner in which the fastener and a cord are used to monitor a patient.

In FIG. 4, there is shown a fragmentary, simplified perspective view of a patient 64 wearing a garment 62 and having the switch 12 fastened to the garment 62 and connected by at least one length of cord to the housing 13 at the patient station. In the preferred embodiment, the switch 12 is fastened by a first length of cord 60 to a switch member (not shown in FIG. 4) that may be pulled from its position in the housing 13 to signal an alarm easier than the switch 12 is freed from the garment 62. The switch member forms a part of the switch 15 (FIG. 1). A second length of cord (not shown in FIG. 4) fastens the switch member to the housing 13 so as to limit its movement.

To connect the switch 12 to the alarm, both the first length and the second length include conductors 36 and 38 (FIGS. 1–3). The second length of cord is firmly fastened to a switch member (not shown in FIG. 4) and to the housing 13 so that it cannot be pulled free and remains electrically connected to a circuit within the housing 13. It should require a force preferably in the range of one-half pound to ten pounds and still more preferably approximately one and one-half pounds to pull the first length of cord 60 and switch member from the housing 13. The first length of cord should be selected for the use but should be within a range of five inches to five feet and preferably within a range of ten inches to twenty inches for a chair and still more preferably 15 inches for a chair. It should be preferably within a range of two feet to three feet for a bed and still more preferably thirty inches.

The alarm switch may be of any type, such as for example the switch disclosed in U.S. Pat. No. 4,160,972, the disclosure of which is incorporated herein by reference when used to activate an alarm when the switch is opened. To activate an alarm when a switch is closed rather than when opened, a source of power in series with the alarm and switch may be used. Moreover, a station voice recording system 14 (FIG. 1) may used with other types of systems such as that disclosed in U.S. Pat. No. 4,577,185, the disclosure of which is incorporated by reference herein, to activate an alarm when the first length of cord and switch member is pulled free from the housing 13 rather than from the garment of a patient. Thus, the cord may pull a ferromagnetic member away from a reed switch or may pull a mechanical switch closed or open or may move an opaque object from or into a location between a light source and a photocell to change the state of a switch and thus activate a voice recording and one or more alarms. The alarms 18 and 20 (FIG. 1) may be audible or visual or both.

With this arrangement, if the patient were to move further away from the housing 13 such as by falling from a chair or leaving a bed, the cord 60 would stretch and pull the switch 12 free, closing a circuit in the housing 13 and thus activate the alarm and/or voice recording. The switch 12 is generally fastened to the torso of a patient such as on a shirt or the top part of a hospital gown or the like in the vicinity of the shoulder and the cord 60 is sized in accordance with the location of the monitoring apparatus. For example, in a wheelchair, the cord 60 is generally 18 inches long and in a bed setting it is generally two feet long. It should be no shorter than one foot and no longer than five feet in length. The housing 13 is generally fastened to a nearby support.

Figure 5:
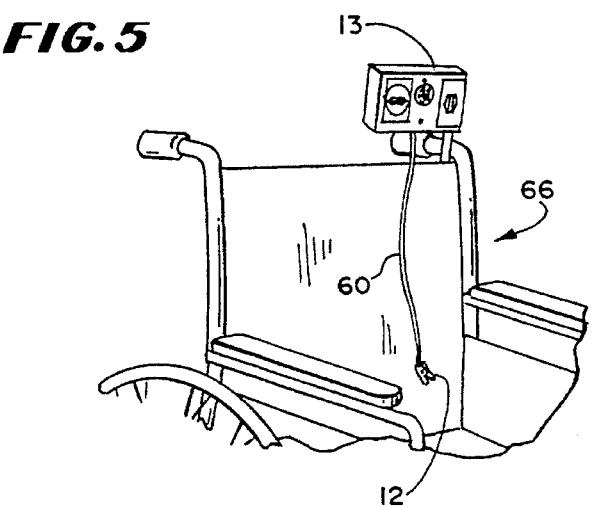
FIG. 5 is a fragmentary simplified perspective view illustrating the use of the patient monitoring system in connection with a wheelchair.

In FIG. 5, there is shown a fragmentary, simplified perspective view of a wheelchair 66 showing an appropriate mounting for the housing 13 above the wheelchair with the cord 60 facing forwardly and being connected to the switch 12 so that a patient in the wheelchair may have the clip 12 fastened to the patient's garment. In the preferred embodiment, the cord is fifteen inches long. If the patient then slumps forward out of the chair, the switch member is pulled free or the alligator clip 12 is pulled free from the garment and causes the housing 13 to provide an alarm signal to a caretaker, preferably at a remote location. The recorded message in an embodiment of this type may request the patient to remain stationary until aid arrives. If the patient removes the alligator clip, the alarm also sounds.

Figure 6:
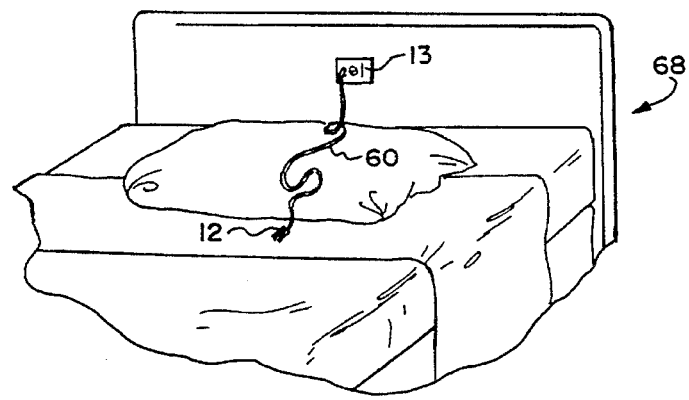
FIG. 6 is a simplified, perspective, fragmentary view illustrating the use of the patient monitoring system in connection with a bed.

In FIG. 6, there is shown a fragmentary simplified view of a bed 68 equipped with a patient's station monitoring housing 13 mounted to the headboard so that the switch 12 can be fastened to a patient. The cord has a length so that if the patient falls from the bed or attempts to leave, the cord 60 will cause either the switch member to be pulled from the housing or the clip 12 to be pulled free from the garment of the patient. In either case, a message may be played requesting the patient to remain in the bed and/or an alarm may be transmitted to a caretaker who can attend to the matter. In the preferred embodiment, the cord is 30 inches long.

Figure 7:
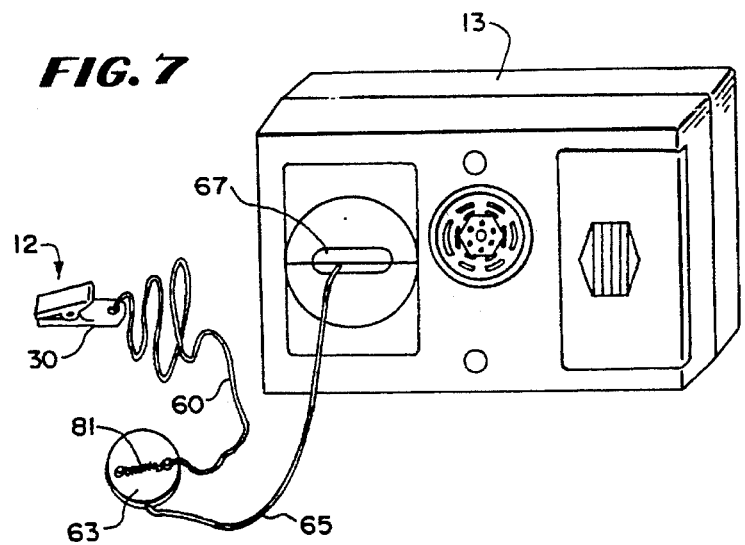
FIG. 7 is a perspective view of an embodiment of the invention.

In FIG. 7, there is shown a perspective view of the switch 12 and housing 13. As shown in this view, the switch 12 includes the alligator clip 30, the first length of cord 60, a switch member 63, and the second length of cord 65 fastened and electrically connected to the housing 13. In this view, the switch member 63 has been pulled free from a slot 67, which in practice causes an alarm to sound. With the switch 12 closed, even if the switch member 63 were in position within the slot 67, the alarm would sound because the alligator clip 30 has been closed.

In FIG. 8, there is shown a simplified, fragmentary, partly-perspective and partly-schematic view of housing 13 and switch 12. The switch 12 includes the first length of the cord 60 and the second length of cord 65 both connected to the switch member 63 so that when the switch member 63 is pulled free from the housing 13, the second cord 65 remains electrically connected. The housing 13 is shown having the second switch 15, a power source 69, the delay 16 and the station alarm 18 as shown in FIG. 1.

In the embodiment of FIG. 8, the switch 15 includes a permanent magnet or an energized electrode magnet 71, a reed relay 73, and ferromagnetic path members 75, 77 and 79. The ferromagnetic path members 75, 77 and 79 form a closed ferromagnetic circuit with the magnet 71. This ferromagnetic circuit maintains the normally open reed switch 73 in its open position. The switch member 63 is ferromagnetic, and when seated so that it rests on the members 75 and 79, forms a ferromagnetic shunt that diverts flux away from the member 77, thus permitting the reed relay 73 to close.

With this arrangement, when the switch 63 closes, a signal is transmitted to the power source 69 through the delay 16 and the station alarm 18 to initiate the voice message from the station voice recording system 14 (FIG. 1) and the station alarm 18 as well as to the remote station alarm 20 as explained in connection with FIG. 1.

However, when switch 12 (FIG. 1) is closed, a closed circuit is formed through the conductors within the cord 60, the conductors connected to them in the continuation of cord at 81 and the continuation of the cord 65 to form an alternate path closing a circuit between the power source 69 and the delay 16 and station alarm 18 so that if the ferromagnetic member 63 jams in place and the alligator clip pulls free, an alarm is nonetheless provided and if someone removes the alligator clip and permits it to close, an alarm is given.

In FIG. 9, a slightly different embodiment of switch 12A and housing 13A is shown having a similar arrangement of switch 12, cord 60, cord 81, cord 65, delay 16 and station alarm 18 as in the embodiment of FIG. 7. However, instead of having the magnet 71 and reed relay 73 that cooperates with a ferromagnetic shunt member 63, the switch 13A includes a light source 71A and a photocell 73A. The member 63A is opaque and need not be ferromagnetic, but when in position, blocks light from the light source 71A to the photocell 73A, but when pulled free, generates a pulse that is applied through the delay 16 and the station alarm 18 to initiate an alarm and a voice message in a manner described in connection with FIG. 1.

Figure 10:
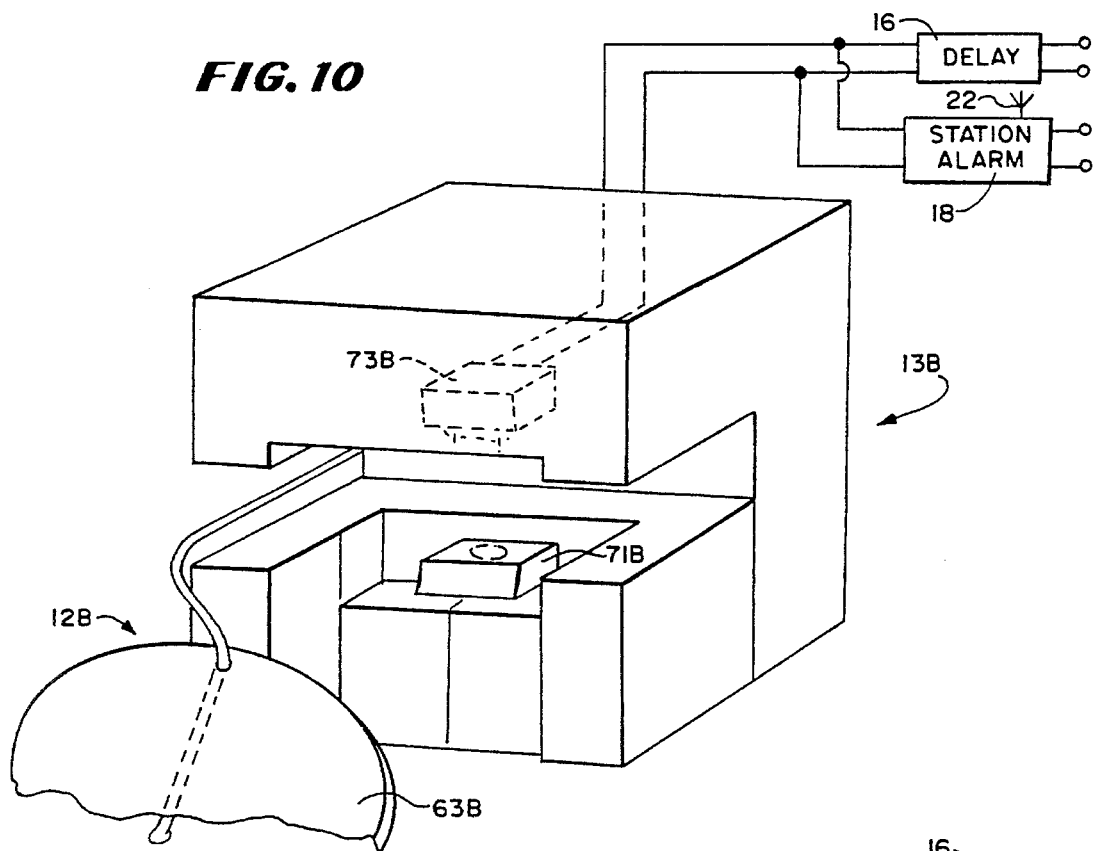
FIG. 10 is a simplified, fragmentary, partly perspective and partly schematic view of still another embodiment of the invention.

In FIG. 10, there is shown a simplified, fragmentary, partly-perspective and partly-schematic view of still another embodiment of switch 12B and housing 13B having the same general arrangement of lengths of cords 60, 81, and 65 and of the delay 16 and station alarm 18 as in the embodiments of FIGS. 8 and 9. However, instead of a ferromagnetic shunt switch or a photoelectric switch, the switch member 63B is a high dielectric constant member such as polyethylene or the like and plates 71B and 73B are capacitive plates connected by a source of AC current.

When the dielectric member 63B is positioned within the plates 71B and 73B, the alternating current potential is dropped across the capacitive element, but when it is removed, the capacitance changes to generate a change in alternating current amplitude. The change is detected by a combination rectifier and differentiator to create a spike and thus energize the alarm. With this arrangement, the circuit works in a manner similar to the embodiments of FIGS. 8 and 9.

Figure 11:
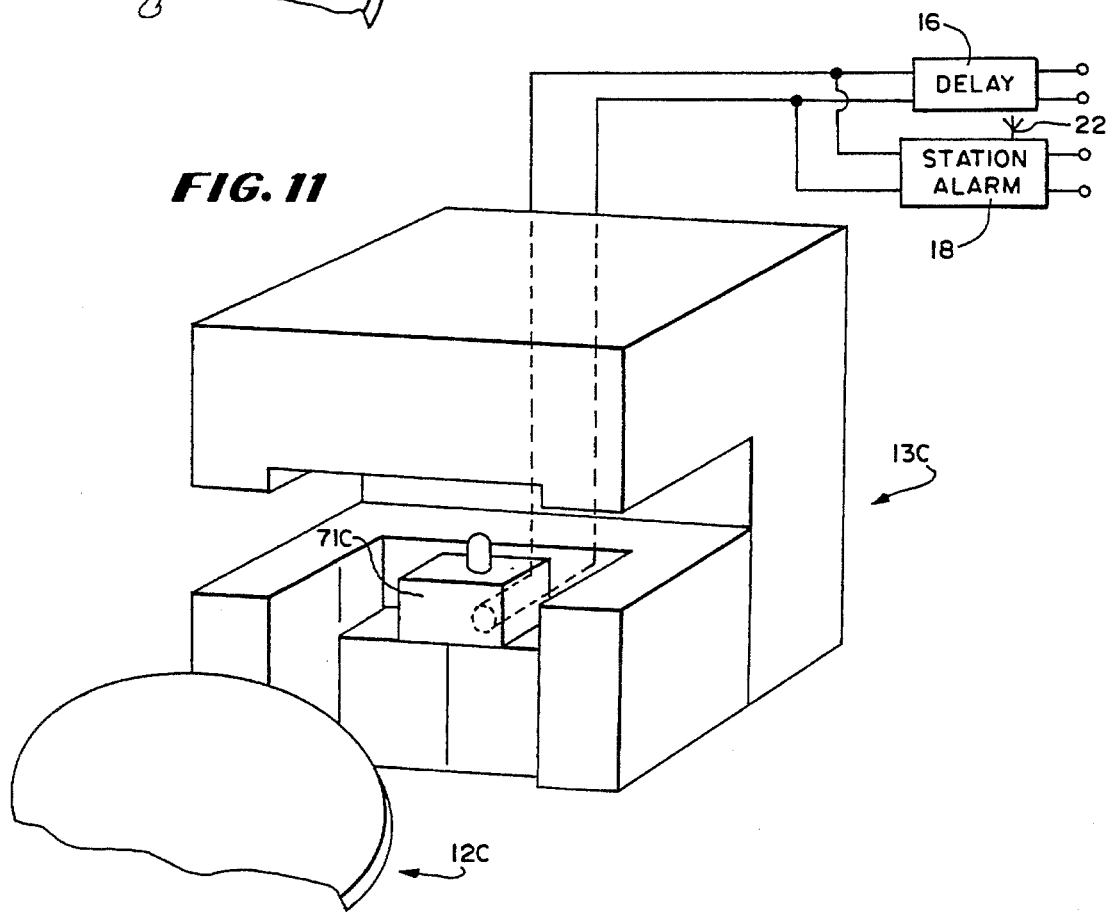
FIG. 11 is a simplified, fragmentary, partly perspective and partly schematic view of still another embodiment of the invention.

In FIG. 11, there is shown still another embodiment of housing 13C and switch 12C having a delay line 16, an alarm 18 and cord lengths 60, 81 and 65 as in the embodiments of FIGS. 8–10. However, in the embodiment of FIG. 11, the switch 12C is any mechanical disk sized to fit within the slot 67 (FIG. 7) and the switch element 71C is a mechanical switch which in the embodiment of FIG. 11 is a tumbler switch with a rotatable switch element that is moved from the on to the off position by the disk 12C. However, a push button switch or a turn switch could also be used spring biased, so that when the disk 12C is removed, the switches are actuated to initiate an alarm, and when inserted, moves the switch to the open position such as by pushing a push button switch or the like.

From the above description, it can be understood that the patient monitoring arrangement of this invention has several advantages, such as for example: (1) it is difficult for a patient to accidentally or intentionally defeat the patient monitoring system by removing the clip; (2) the system may provide a tailored statement when the patient removes the clip, designed to achieve the desired effect such as the patient waiting or returning to bed or the like until a caretaker arrives; and (3) the fastener is relatively simple and inexpensive.

Although a preferred embodiment of the invention has been described with some particularity, many modifications and variations of the preferred embodiment are possible within the light of the above teachings. Therefore, it is to be understood that, within the scope of the appended claims, the invention may be practiced other than as specifically described.

What is claimed is:

1. A method of monitoring a patient comprising the steps of:
    fastening a first switch at a first end of an elongated flexible member to a patient and connecting a second end of the flexible member to a second switch wherein when the patient moves beyond a predetermined length, one of the first switch and the second switch is moved from one of an open and a closed position to the other of an open and a closed position; and
    activating a monitoring station when one of the first switch and the second switch is moved, wherein an alarm is provided and a voice message is announced in the vicinity of the patient.

2. A method in accordance with claim 1 in which an alarm is provided to a caretaker.

3. A method of monitoring a patient, comprising the steps of:
    fastening a combined electrical switch and clip at a first end of an elongated flexible member to a patient and connecting a second end of the flexible member to a second switch, wherein if the patient moves beyond a predetermined distance, one of the combined switch and clip is pulled free from the patient and the second switch is activated resulting in a change in the first or second switch between one of an open state or a closed state to the other of the open or closed state;
    providing an alarm signal when the combined clip and switch is moved to the other of the open or closed state; and
    a predetermined time after said alarm signal is initiated providing a verbal message.

4. A method in accordance with claim 3 in which the step of fastening the switch and clip to a patient includes the step of fastening a combined electrical switch and alligator clip to the clothing of the patient.

5. Apparatus for monitoring a patient, comprising:
    a control housing mounted to a patient station;
    a flexible member attached to the control housing;
    said flexible member including first and second electrical conductors insulated from each other;
    a fastening means;
    one end of the flexible member being connected to the fastening means, said fastening means being adapted to move from a first position to a second position;
    the first position being one of having the first and second electrical conductors electrically in contact with each other and the second position being one of having the first and second conductors electrically separated from each other;
    a movable switch means;
    said movable switch means being removably mounted in the control housing;
    the control housing including means for providing an alarm signal when one of the fastening means moves from the second position to the first position and the movable switch means is removed from said housing, whereby a caretaker is informed by the alarm when the patient moves beyond a predetermined distance.

6. Apparatus for monitoring a patient in accordance with claim 5 in which:
    said fastening means includes an alligator clip;
    said alligator clip having first and second jaws;
    said first and second jaws including means for electrically connecting said first and second conductors together in one of an open position and a closed position.

7. Apparatus in accordance with claim 6 in which said alligator clip includes spring means for biasing said jaws in a closed position.

8. Apparatus in accordance with claim 6 in which said alarm includes a first signal means and a second signal means, said second signal means being a recorded voice message sounding within hearing distance of a patient to which said alligator clip has been fastened.

9. Apparatus in accordance with claim 6 in which said first position is a position in which the first and second conductors are in electrical contact with each other and the second position is a position in which they are separated from each other.

10. Apparatus in accordance with claim 8 further including a delay line in circuit with said switches and said second signal means.

* * * * *